United States Patent [19]

Andersson et al.

[11] Patent Number: 4,971,054
[45] Date of Patent: Nov. 20, 1990

[54] BREATHING VALVE

[75] Inventors: Gillis Andersson, Danderyd; Roland Friberg, Sollentuna; Per Ljungqvist, Karlstad, all of Sweden

[73] Assignee: Respaid AB, Farsta, Sweden

[21] Appl. No.: 300,584

[22] Filed: Jan. 23, 1989

[30] Foreign Application Priority Data

Jan. 22, 1988 [SE] Sweden ............................. 8800203

[51] Int. Cl.⁵ .............................................. A61M 16/00
[52] U.S. Cl. ............................ 128/207.16; 128/207.14
[58] Field of Search ................... 128/207.14, 207.15, 128/207.6; 623/9

[56] References Cited

U.S. PATENT DOCUMENTS

| | | | |
|---|---|---|---|
| 2,804,076 | 8/1957 | Giraudon | 128/207.16 |
| 3,066,674 | 12/1962 | Capra | 128/207.16 |
| 3,137,299 | 6/1964 | Tabor | 623/9 |
| 3,683,931 | 8/1972 | Chelucci et al. | 128/207.16 |
| 3,827,440 | 8/1974 | Birch et al. | 128/207.16 |
| 4,044,793 | 8/1977 | Krueger et al. | 128/207.15 |
| 4,064,882 | 12/1977 | Johnson et al. | 128/207.15 |
| 4,538,607 | 9/1985 | Saul | 128/207.16 |
| 4,759,356 | 7/1988 | Muir | 128/207.16 |
| 4,763,645 | 8/1988 | Kapp | 128/207.14 |
| 4,774,945 | 10/1988 | White et al. | 623/9 |
| 4,809,693 | 3/1989 | Rangoni et al. | 128/207.16 |
| 4,817,598 | 4/1989 | La Bombard | 128/207.14 |

FOREIGN PATENT DOCUMENTS 389470  9/1908  France ..................... 623/9

*Primary Examiner*—Edgar S. Burr
*Assistant Examiner*—Aaron J. Lewis
*Attorney, Agent, or Firm*—Walter Ottesen

[57] ABSTRACT

The invention is directed to a breathing valve for patients requiring humidication and filtration of breathing air inhaled via tracheostomas and tracheal tubes. The breathing valve includes a valve body, a filter removably placeable inside the valve body, a cup-shaped cap attached over the opening of the valve body and a disc-shaped membrane disposed in front of the filter in the path of the inspired air. The breathing valve is intended to be a complete system. The system can be easily disassembled and components can be replaced by the user as required and this applies especially to the filter.

12 Claims, 1 Drawing Sheet

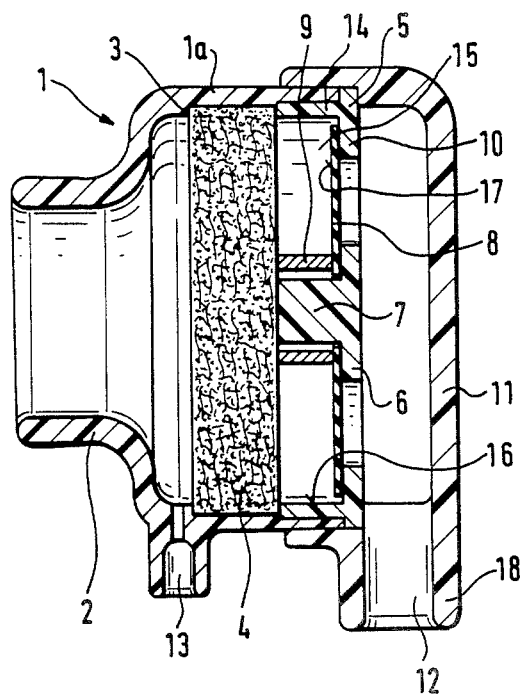

BREATHING VALVE

The invention relates to a breathing valve for patients requiring humidification and filtration of breathing air inhaled via tracheostomas and tracheal tubes.

The area of application of breathing valves of the type in question is for patients with reduced respiratory capacity who need to use a ventilator in combination with tailored tubing systems for the remainder of their lives. The need for a breathing valve is particularly accentuated in patients with sufficient respiratory capacity remaining so that use of the ventilator can be limited to the nighttime while breathing during the daytime can take place via a tracheostoma and a tracheal tube or via the normal respiratory passages.

If the patient cannot breathe through his natural respiratory passages during the daytime, he must breathe through the tracheal tube. The air inhaled by the patient via a tube of the currently known type is not filtered or humidified in the same way as the air inhaled via the natural respiratory passages, nose and mouth.

SUMMARY OF THE INVENTION

It is an object of the invention to overcome the above-described limitations. The breathing valve of the invention includes a valve body, a filter mounted inside the valve body so as to be replaceable by the patient, a cup-shaped cap removably fastened over the inlet opening to the valve body and a disc-shaped membrane placed inside the valve body in front of the filter in the path of the inspiration air.

BRIEF DESCRIPTION OF THE DRAWING

The invention will be described in greater detail in conjunction with the appended drawing, which shows a longitudinal section through an embodiment of a breating valve according to the invention.

DESCRIPTION OF THE PREFERRED EMBODIMENTS OF THE INVENTION

The breathing valve 1 is intended to be attached to a tracheal tube, and valve body 1a is provided for this purpose with a tapered tubular stub 2 whose diameter and length are dimensioned to fit snugly into the similarly tapered terminal portion of the tracheal tube. These dimensions are standardized as a rule. Valve body 1a is provided with an annular shoulder 3 extending around its inner wall on which the filter 4 is seated so as to be in seal-tight contact engagement therewith. The filter 4 is made of a material known as cell plastic which is commercially available from Jacopac AB, a corporation organized and doing business under the laws of Sweden and located in Nora, Sweden.

The cup-shaped cap 5 ont eh valve body 1a has a perforated base wall 6. In teh center of the inside of this perforated base wall there is a neck 7 on which a disc-shaped membrane 8 is fastened by means of a retaining ring 9 slipped around the neck 7. In the unactuated state, teh peripheral edge of the membrane 8 seals against a lip 10 in the cap base wall 6. When the cap 5 is fastened to the valve body 1a, its circular rim 14 will lie up against the filter 4 in the body 1a and fix the filter 4 in place. The breathing valve is thereby assembled and can be attached to a tarcheal tube for use.

On inhalation, air flows in through the perforated base wall 6 of the cap 5. The membrane 8 lifts from teh lip 10 and air flows through teh filter 4 on which moisture has condensed and thereby humidifies the air as it moves toward the tube and down into the patient's lungs.

As mentioned above, the purpose of the filter 4 is to filter and humidify the inspiration air. It is located in the valve body 1a in such a way that at least a portion of the expiration air from the lungs, containing a substantial amount of moisture, swirls around in the valve body 1a behind the membrane 8, which acts as a check valve, whereby the moisture-ladened exhaled air will also pass through the filter 4 and automatically humidify the same on its way out through the natural respiratory passages of the patient. The exhaled air swirls around in the chamber 15 and the moisture therein also condenses on the inner wall surface 16 of chamber 15 and on the inside wall surface 17 of the membrane 8 and this condensed moisture too contributes to humidifying the inhaled air passing through the valve body 1a and filter 4.

In cold weather, the respiration air should be preheated. According to another feature of the invention, the breathing valve 1 can therefore be equipped with a preheating shield 11, which is attached to the outer part of the valve body 1a over the valve cap 5. The shield 11 has an opening in the form of a downwardly-directed conduit 18 defining inspiration channel 12, which enables the patient's body heat to be used to preheat the inspiration air.

In addition to the preheating shield 11, the valve body 1a is also equipped with a nipple 13 for connection to an oxygen cylinder.

The breathing valve in accordance with the invention is primarily intended to be used as a speaking valve. It should therefore prepare the inspiration air to as great an extent as possible in the same way as the normal respiratory passages prepare the air, that is, the air should be preheated, filtered and humidified. In addition, the check valve should exert as little inspiration resistance as possible as it closes immediately when the pressure on its inside exceeds the pressure on its outside, in order to prevent a hissing or whistling sound while the patient is exhaling or speaking.

The breathing valve in accordance with the invention is intended to be a complete system, but the components of the valve can nevertheless be easily disassembled and replaced by the user, if necessary, especially the filter 4.

The valve body 1a is configured in such a manner that it can easily be attached to a tracheal tube, which generally has a standardized inlet opening.

The membrane 8, which acts as a check valve, exerts as little breathing resistance as possible at the same time as it closes immediately when the patient exhales or wishes to speak. It is thereby essential that closure take place immediately in order to prevent a hissing or whistling sound.

The filter 4 fixed inside the valve body 1a by means of the cup-shaped valve body cap 5 is easily replaceable, even by the patient.

The breathing valve provides optimal throughflow which results in extremely low breathing resistance.

The membrane-type check valve closes immediately on expiration, eliminating all hissing and whistling sounds, which is essential for the patient's well-being.

The filter 4 is held in place by the valve body cap 5 and is thereby replaceable. This enables the patient to reside and work on dusty premises, even for an extended period of time.

The nipple provided on the valve body 1a permits a connection to an oxygen cylinder to be made and the preheating shield 11 that can be mounted on the outer part of the valve body 1a completes the system.

It is understood that the foregoing description is that of the preferred embodiments of the invention and that various changes and modifications may be made thereto without departing from the spirit and scope of the invention as defined in the appended claims.

What is claimed is:

1. A breathing valve such as a speaking valve for patient inhaling air via the tracheostomas and tarchea which must be humidified and filtered, the breathing valve comprising:
   an annular valve body having an inner wall surface defining a passage for passing air to the respiratory system of the patient,
   check valve means dispsoed in said passage for opening when teh patient inhales and closing when teh patient exhales;
   said check valve means including: a support member mounted on said valve body; aperture means formed in said support member for conducting inhaled breathing air into said passage; and, an unbiased membrane mounted on said support member for coactingwith said aperture means to open the latter for admitting the inhaled air and for immediately closing said aperture means during exhalation;
   filter means for filtering and humidifying air inhaled by the patient, said filter means being dispsoed in said passage downstream fo said membrane when viewed in teh direction of flow of teh inhaled air;
   said membrane and said filter means conjointly defining an unobstructed chamber extending a predetermined distance therebetween in said valve body when said membrane closes said aperture means to permit moisture ladened exhaled air to pass through said filter means and swirl around in said chamber causing moisture to condense on said filter means and in said chamber thereby making the condensed moisture available for humidifying the inhaled air upon teh next inhalation;
   seat means formed in said passage for receiving said filter means thereon;
   holding means for holding said filter means in contact engagement with said seat means when said support member is mounted on said valve body; and,
   said holding means being formed on said support member so as to hold said filter means at said distance from said membrane to define said chamber.

2. The breathing valve of claim 1, said valve body having an end portion upstream of said filter means and said support member being a cup-shaped cap removably seated in said end portion; said cup-shaped cap having a base wall containing said aperture means and a rim extending from said base wall to said filter means to define said holding means.

3. The breathing valve of claim 2, said check valve means further including fastening means disposed centrally on said support member for fastening said membrane thereto.

4. The breathing valve of claim 1, oxygen connection means formed on said valve body for facilitating the connection of an oxygen supply to admit oxygen into said passage.

5. The breathing valve of claim 2, comprising a preheating shield attached to said valve body over said cap; and, said shield defining a conduit for conducting the inhaled air to said check valve, said conduit being placeable in contact engagement with the body of the patient so as to transfer the heat of the body to the inhaled breathing air passing therethrough to said check valve.

6. The breathing valve of claim 1, said filter means being spaced from said membrane so as to define said chamber therebetween in said annular body for permitting at least a portion of the moisture-ladened air exhaled by the patient to swirl about in said chamber before passing back out of the filter and to the ambient via the natural respiratory system of the patient.

7. A breathing valve such as a speaking valve for a patient inhaling air via the tracheostomas and tarchea which must be humidified and filtered, the breathing valve comprising:
   an annular valve body having an inner wall surface defining a passage for passing air to the respiratory system of teh patient;
   check valve means dispsoed in said passage for opening when teh patient inhales and closing when teh patient exhales;
   said check valve means including: a support member mounted on said valve body; aperture means formed in said support member for conducting inhaled breathing air into said passage; and, a membrane having an inside surface and an outside surafce and being mounted on said support member for coating with said aperture means to open the latter for admitting the inhaled air and for immediately closing said aperture means during exhalation;
   said support member defining a flat surface for receiving said membrane thereagainst at said outside surafce when said membrane closes said aperture means during exhalation thereby causing said membrane to lie in a single plane coplanar with said flat surface;
   said membrane mounted on said flat surafce so as to close immediately when the pressure on asid inside surafce exceeds the pressure on said outside surafce thereby preventing a hissing sound while the patient is exhaling or speaking;
   filter means for filtering and humidifying air inhaled by the patient, said filter means being disposed in said passage downstream of said membrane when viewed in teh direction of flow of the inhaled air;
   said membrane and said filter means conjointly defining a clear unobstructed chamber extending a predetermined distance therebetween in said valve body when said membrane closes said aperture means to permit moisture ladened exhaled air to pass through said filter means and siwrl around in said chamber causing moisture to condense on said filter means and in said chamber thereby making the condensed moisture available for humidifying the inhaled air upon teh next inhalation;
   seat mans formed in said passage for receiving said filter means thereon; and,
   holding means for holding said filter means in contact engagement with said seat means when said support member is mounted on said valve body, said holding means being formed at said support member so as to hold said filter means at said distance from said membrane to define said chamber.

8. The breathing valve of claim 7, said valve body having an end portion upstream of said filter means and said support member being a cup-shaped cap removably seated in said end portion; said cup-shaped cap having a base wall containing said aperture means and a rim extending from said base wall to said filter means to define said holding means.

9. The breathing valve of claim 8, said check valve means further including fastening means disposed centrally on said support member for fastening said membrane thereto.

10. The breathing valve of claim 7, oxygen connection means formed on said valve body for facilitating the connection of an oxygen supply to admit oxygen into said passage.

11. The breathing valve of claim 8, comprising a preheating shield attached to said valve body over said cap; and, said shield defining a conduit for conducting the inhaled air to said check valve, said conduit being placeable in contact engagement with the body of the patient so as to transfer the heat of the body to the inhaled breathing air passing therethrough to said check valve.

12. The breathing valve of claim 7, said filter means being spaced from said membrane so as to define said chamber therebetween in said annular body for permitting at least a portion of the moisture-ladened air exhaled by the patient to swirl about in said chamber before passing back out of the filter and to the ambient via the natural respiratory system of teh patient.

* * * * *

UNITED STATES PATENT AND TRADEMARK OFFICE
CERTIFICATE OF CORRECTION

PATENT NO. : 4,971,054

DATED : November 20, 1990

INVENTOR(S) : Gillis Andersson, Roland Friberg and Per Ljungqvist

It is certified that error appears in the above-identified patent and that said Letters Patent is hereby corrected as shown below:

In column 1, after the title: insert the following: BACKGROUND OF THE INVENTION --.

In column 1, line 37: delete "breat-" and substitute -- breath- -- therefor.

In column 1, line 55: delete "ont eh" and substitute -- on the -- therefor.

In column 1, line 56: delete "teh" and substitute -- the -- therefor.

In column 1, line 60: delete "teh" and substitute -- the -- therefor.

In column 1, line 65: delete "tarcheal" and substitute -- tracheal -- therefor.

In column 1, line 67: delete "teh" and substitute -- the -- therefor.

In column 1, line 68: delete "teh" and substitute -- the -- therefor.

In column 3, line 12: before "patient", please add -- a --.

UNITED STATES PATENT AND TRADEMARK OFFICE
CERTIFICATE OF CORRECTION

PATENT NO. : 4,971,054

DATED : November 20, 1990

INVENTOR(S) : Gillis Andersson, Roland Friberg and Per Ljungqvist

It is certified that error appears in the above-identified patent and that said Letters Patent is hereby corrected as shown below:

In column 3, line 12: delete "tarchea" and substitute -- trachea -- therefor.

In column 3, line 17: delete "patient," and substitute -- patient; -- therefor.

In column 3, line 18: delete "dispsoed" and substitute -- disposed -- therefor.

In column 3, line 19: delete "teh" and substitute -- the -- therefor (two occurrences).

In column 3, line 31: delete "dispsoed" and substitute -- disposed -- therefor.

In column 3, line 32: delete "fo" and substitute -- of -- therefor.

In column 3, line 33: delete "teh" and substitute -- the -- therefor (two occurrences).

In column 3, line 43: delete "teh" and substitute -- the -- therefor.

In column 4, line 14: delete "tarchea" and substitute -- trachea -- therefor.

UNITED STATES PATENT AND TRADEMARK OFFICE
CERTIFICATE OF CORRECTION

PATENT NO. : 4,971,054

DATED : November 20, 1990

INVENTOR(S) : Gillis Andersson, Roland Friberg and Per Ljungqvist

It is certified that error appears in the above-identified patent and that said Letters Patent is hereby corrected as shown below:

In column 4, line 19: delete "teh" and substitute -- the -- therefor.

In column 4, line 21: delete "teh" and substitute -- the -- therefor (two occurrences).

In column 4, line 27: delete "su-".

In column 4, line 28: delete "rafce" and substitute -- surface -- therefor.

In column 4, line 29: delete "coating" and substitute -- coacting -- therefor.

In column 4, line 35: delete "surafce" and substitute -- surface -- therefor.

In column 4, line 39: delete "surafce" and substitute -- surface -- therefor.

In column 4, line 40: delete "asid" and substitute -- said -- therefor.

In column 4, line 41: delete "surafce" and substitute -- surface -- therefor.

UNITED STATES PATENT AND TRADEMARK OFFICE
CERTIFICATE OF CORRECTION

PATENT NO. : 4,971,054  Page 4 of 4

DATED : November 20, 1990

INVENTOR(S) : Gillis Andersson, Roland Friberg and Per Ljungqvist

It is certified that error appears in the above-identified patent and that said Letters Patent is hereby corrected as shown below:

In column 4, line 47: delete "teh" and substitute -- the -- therefor.

In column 4, line 53: delete "siwrl" and substitute -- swirl -- therefor.

In column 4, line 57: delete "teh" and substitute -- the -- therefor.

In column 6, line 13: delete "teh" and substitute -- the -- therefor.

Signed and Sealed this

Twenty-eighth Day of April, 1992

Attest:

HARRY F. MANBECK, JR.

*Attesting Officer*  *Commissioner of Patents and Trademarks*